ations,

United States Patent [19]
Kurihara et al.

[11] Patent Number: 5,808,032
[45] Date of Patent: Sep. 15, 1998

[54] ANTI-HBS ANTIBODY GENES AND EXPRESSION PLASMIDS THEREFOR

[75] Inventors: Tatsuya Kurihara, Osaka; Shigekazu Matsukura, Tochigi-ken; Nobuo Tsuruoka, Osaka; Kenji Arima, Tokyo; Tatsuro Nishihara, Kanagawa-ken, all of Japan

[73] Assignee: Suntory Limited, Osaka, Japan

[21] Appl. No.: 157,101

[22] PCT Filed: Mar. 30, 1993

[86] PCT No.: PCT/JP93/00396

§ 371 Date: Apr. 5, 1994

§ 102(e) Date: Apr. 5, 1994

[87] PCT Pub. No.: WO93/20205

PCT Pub. Date: Oct. 14, 1993

[30] Foreign Application Priority Data

Mar. 30, 1992 [JP] Japan ................................ 4-074678

[51] Int. Cl.⁶ ............................ C12N 15/13; C07H 21/04
[52] U.S. Cl. ................................. 536/23.53; 435/320.1; 435/91; 530/387.3; 530/388.3; 530/387.1; 530/389.4
[58] Field of Search ................. 530/388.3, 387.1, 530/389.4; 536/23.53; 435/320.1, 91

[56] References Cited

FOREIGN PATENT DOCUMENTS

89/12092 4/1989 WIPO ............................. C12N 15/00
89/12098 12/1989 WIPO ............................. C12N 9/64

OTHER PUBLICATIONS

Riechmann et al. [Nature 332:323–327 (1988)].

Waldmann [Science 252:1657–1662 (1991)].

Harris et al. [TIBTECH 11:42–44 (1993)].

Osband et al. [Immunotherapy 11(6):193–195 (1990)].

Dillman [Ann, Internal Med. 111:592–600 (1989)].

Hird et al. [Genes and Cancer (1990) chapter 17].

Curti [Critical Reviews in Oncology/Hematology 14:29–39 (1993)].

Peterson et al. [J.I. 132(2):920–927 (1984)].

GeneBank report pp. 14, 15, 29 and 30.

Primary Examiner—Frank C. Eisenschenk
Attorney, Agent, or Firm—Cushman, Darby & Cushman IP Group of Pillsbury, Madison & Sutro, LLP

[57] ABSTRACT

The L and H chains of the human anti-HBs antibody can be produced by the genetic recombination techniques to provide the desired human anti-HBs antibody easily on a large scale. The invention relates to nucleotide base sequences coding for the respective polypeptides that constitute the L and H chains of the anti-HBs antibody, expression plasmids containing them, and transformants prepared by transformation with the expression plasmids.

4 Claims, 18 Drawing Sheets

Fig. 4(a)

```
         10        20        30        40        50        60
GGGGGGGAATCAGTCCCACTCAGGACACAGCATGGACATGAGGGTCCCCGCTCAGCTCC
                                 MetAspMetArgValProAlaGlnLeuL
                                 -22       -20

70        80        90       100       110       120
TGGGGCTCCTGCTGCTCTGGTTCCCAGGTGCCAGGTGTGACATCCAGATGACCCAGTCTC
euGlyLeuLeuLeuLeuTrpPheProGlyAlaArgCysAspIleGlnMetThrGlnSerP
-10                                            -1 +1

130       140       150       160       170       180
CATCTGCCATGGCTGCATCTGTAGGAGACAGAGTCACCATCACTTGTCGGGCGAGTCAGG
roSerAlaMetAlaAlaSerValGlyAspArgValThrIleThrCysArgAlaSerGlnG
          10                                   20

190       200       210       220       230       240
GCATTGGCAATTATTTAGTCTGGTTTCAGCAGAAACCAGGGAAAGTCCCTAAGCGCCTGA
lyIleGlyAsnTyrLeuValTrpPheGlnGlnLysProGlyLysValProLysArgLeuI
        30                                       40
```

Fig. 4(b)

```
         250       260       270       280       290       300
TCTATGCTGCATCCAGTTGCAAAGTGGGGTCCCATCGAGTTCAGGGCAGTGGATCTG
 IeTyrAlaAlaSerLeuGlnSerGlyValProSerArgPheSerGlySerG
                                50                        60

310       320       330       340       350       360
GGACAGAATTCACTCTCACAATCAGCAGACTGCAGCCTGAAGATTTTGCAACTTATTACT
 lyThrGluPheThrLeuThrIleSerArgLeuGlnProGluAspPheAlaThrTyrTyrC
                70                                 80

370       380       390       400       410       420
GTCTACATCATAATAATTACCCGCTAAGTTTCGGCGAGGACCAAGGTGGAGATCAAAC
 ysLeuHisHisAsnAsnTyrProLeuSerPheGlyGlyThrLysValGluIleLysA
                90                                100

430       440       450       460       470       480
GAACTGTGGCTGCACCATCTGTCTTCATCTTCCCGCCATCTGATGAGCCAGTTGAAATCTG
 rgThrValAlaAlaProSerValPheIlePheProProSerAspGluGlnLeuLysSerG
                110                               120

490       500       510       520       530       540
GAACTGCCTCGTGTTGTGTGCCTGCTGAATAACTTCTATCCCAGAGAGGCCAAAGTACAGT
 lyThrAlaSerValValCysLeuLeuAsnAsnPheTyrProArgGluAlaLysValGlnT
                130                               140
```

Fig. 5(a)

```
         550        560        570        580        590        600
GGAAGGTGGATAAACGCCCTCCAATCGGGTAACTCCCAGGAGAGTGTCACAGAGCAGGACA
rpLysValAspAsnAlaLeuGlnSerGlyAsnSerGlnGluSerValThrGluGlnAspS
           150                                 160

610        620        630        640        650        660
G;CAAGGACACAGCACCTACAGCCTCAGCAGCACCCTGACGCTGAGCAAAGCAGACTACGAGA
erLysAspSerThrTyrSerLeuSerSerThrLeuThrLeuSerLysAlaAspTyrGluL
           170                                 180

670        680        690        700        710        720
AACACAAAGTCTACGCCTGCGAAGTCACCCATCAGGGCCTGAGCTCGCCCGTCACAAAGA
ysHisLysValTyrAlaCysGluValThrHisGlnGlyLeuSerSerProValThrLysS
           190                                 200

730        740        750        760        770        780
GCTTCAACAGGGGAGAGTGTTAGAGGGAGAAGTGCCCCACCTGCTCCTCAGTTCCAGCC
erPheAsnArgGlyGluCys
         210        214
```

Fig. 5(b)

```
         790         800         810         820         830         840
TGACCCCCTCCCATCCTTTGGCCCTCTGACCCTTTTCCACAGGGGACCTACCCCTATTGC 850         860         870         880         890         900
GGTCCTCCAGCTCATCTTCACCTCACCCCCCTCCTCCTTGGCTTTAATTATGCTAA 910         920         930         940         950         960
TGTTGGAGGAGAATGAATAAAGTGAATCTTTGCAAAAAAAAAAAAAAAAAAA 970         980         990        1000        1010        1020
AAAAAAAAAAAAAAAAAAAAAAAAAAAAAAAAAAAAAAAAAAAAAAAAAAAA 1030        1040        1050        1060
AAAAAAAAAAAAAAAAAAAGTACCTTCTGAGGCGGGAAAGAACCAG
```

Fig. 6(a)

```
         10        20        30        40        50        60
GGGGGGGGGGTCGTTGGCCTTTAAGAGGTGTCCAGTGTCAGGTGCAGCTGGTGGAGT
                   ValGlyLeuLeuArgGlyValGlnCysGlnValGlnLeuValGluS
                   -9                                       -1+1

70        80        90       100       110       120
CTGGGGGAGGCGTGGTCCAGCCTGGGAGGTCCCTGAGACTCTCCTGTGCAGCCTCTGGAT
erGlyGlyGlyValValGlnProGlyArgSerLeuArgSerCysAlaAlaSerGlyP
                10                                    20

130       140       150       160       170       180
TCACCTTCAGTAGCAATTCTATGCACTGGGTCCGCCAGGCTCCAGGCAAGGGTTGGAGT
heThrPheSerSerAsnSerMetHisTrpValArgGlnAlaProGlyLysGlyLeuGluT
         30                                    40

190       200       210       220       230       240
GGGTGGCAGTTATATTATATGATGGAAATCATAAATTCTACGCAGACTCCGTGAAGGGCC
rpValAlaValIleLeuTyrAspGlyAsnHisLysPheTyrAlaAspSerValLysGlyA
                50                                    60

250       260       270       280       290       300
GATTCACCATTTCCAGAGACAATTCCAAGAACACACTGTATCTGGAAGTGAAGAGCCTGC
rgPheThrIleSerArgAspAsnSerLysAsnThrLeuTyrLeuGluValLysSerLeuG
         70                                    80
```

Fig. 6(b)

```
         310        320        330        340        350        360
AAACTGAGGACACGGGGTGTCTATTACTGTATAAGAGATCAAACTTACGGAGTCCACAGAT
lnThrGluAspThrGlyValTyrTyrCysIleArgAspGlnThrTyrGlyValHisArgP
                                    90                      100

370        380        390        400        410        420
TTGACTCCTGGGGCCAGGAACCCTGGTCACCGTCTCCTCAGCCTCCACCAAGGGCCCAT
heAspSerTrpGlyGlnGlyThrLeuValThrValSerSerAlaSerThrLysGlyProS
          110                                 120

430        440        450        460        470        480
CGGTCTTCCCCCTGGCACCCTCCTCCAAGAGCACCTCTGGGGGCACAGCGGCCCTGGGCT
erValPheProLeuAlaProSerSerLysSerThrSerGlyGlyThrAlaAlaLeuGlyC
          130                                 140

490        500        510        520        530        540
GCCTGGTCAAGGACTACTTCCCCGAACCGGTGACGGTGTCGTGGAACTCAGGCGCCCTGG
ysLeuValLysAspTyrPheProGluProValThrValSerTrpAsnSerGlyAlaLeuA
          150                                 160
```

Fig. 7(a)

```
        550       560       570       580       590       600
CCAGCGGCGTGCACACCTTCCCGGCTGTCCTACAGTCCTCAGGACTCCTACTCCCTCAGCA
laSerGlyValHisThrPheProAlaValLeuGlnSerSerGlyLeuTyrSerLeuSers
                                                 180

610       620       630       640       650       660
GCGTGGTGACCGTGCCCTCCAGCAGCTTGGGCACCCAGACCTACATCTGCAACGTGAATC
erValValThrValProSerSerSerLeuGlyThrGlnThrTyrIleCysAsnValAsnH
                 190                                  200

670       680       690       700       710       720
ACAAGCCCAGCAACACCAAGGTGGACAAGAAAGTTGAGCCCAAATCTTGTGACAAAACTC
isLysProSerAsnThrLysValAspLysLysValGluProLysSerCysAspLysThrH
                 210                                  220

730       740       750       760       770       780
ACACATGCCCACCGTGCCCAGCACCTGAACTCCTGGGGGACCGTCAGTCTTCCTCTTCC
isThrCysProProCysProAlaProGluLeuLeuGlyGlyProSerValPheLeuPheP
                 230                                  240

790       800       810       820       830       840
CCCCAAAACCCAAGGACACCCTCATGATCTCCCGGACCCCTGAGGTCACATGCGTGGTGG
roProLysProLysAspThrLeuMetIleSerArgThrProGluValThrCysValValV
         250                                  260
```

Fig. 7(b)

```
       850        860        870        880        890        900
TGGACGTGAGCCACGAAGACCCTGAGGTCAAGTTCAACTGGTACGTGGACGGCGTGGAGG
 alAspValSerHisGluAspProGluValLysPheAsnTrpTyrValAspGlyValGluV
                            270                        280

910        920        930        940        950        960
TGCATAATGCCAAGACAAAGCCGCGGGAGGAGCAGTACAACAGCACGTACCGGGTGGTCA
 alHisAsnAlaLysThrLysProArgGluGluGlnTyrAsnSerThrTyrArgValValS
                            290                        300

970        980        990       1000       1010       1020
GCGTCCTCACCGTCCTGCACCAGGACTGGCTGAATGGCAAGGAGTACAAGTGCAAGGTCT
 erValLeuThrValLeuHisGlnAspTrpLeuAsnGlyLysGluTyrLysCysLysValS
                            310                        320

1030       1040       1050       1060       1070       1080
CCAACAAAGCCCTCCCAGCCCCCATCGAGAAAACCATCTCCAAAGCCAAAGGGCAGCCCC
 erAsnLysAlaLeuProAlaProIleGluLysThrIleSerLysAlaLysGlyGlnProA
                            330                        340

1090       1100       1110       1120       1130       1140
GAGAACCACAGGTGTACACCCTGCCCCCATCCCGGGATGAGCTGACCAAGAACCAGGTCA
 rgGluProGlnValTyrThrLeuProProSerArgAspGluLeuThrLysAsnGlnValS
                            350                        360
```

Fig.8(a)

```
          1150        1160        1170        1180        1190        1200
GCCTGACCTGCCTGGTCAAAGGCTTCTATCCAGCGACATGCCGTGGAGTGGGAGAGCA
erLeuThrCysLeuValLysGlyPheTyrProSerAspIleAlaValGluTrpGluSerA
                                       380

1210        1220        1230        1240        1250        1260
ATGGGCAGCCGGAGAACAACTACAAGACCACGCCTCCCGTGCTGGACTCCGACGGCTCCT
snGlyGlnProGluAsnAsnTyrLysThrThrProProValLeuAspSerAspGlySerP
               390                                    400

1270        1280        1290        1300        1310        1320
TCTTCCTCTACAGCAAGCTCACCGTGGACAAGAGCAGGTGGCAGCAGGGGAACGTCTTCT
heLeuTyrSerLysLeuThrValAspLysSerArgTrpGlnGlnGlyAsnValPheS
            410                                    420

1330        1340        1350        1360        1370        1380
CATGCTCCGTGATGCATGAGGCTCTGCACAACCACTACACGCAGAAGAGCCTCTCCCTGT
erCysSerValMetHisGluAlaLeuHisAsnHisTyrThrGlnLysSerLeuSerLeuS
              430                                    440
```

Fig.8(b)

```
         1390      1400      1410      1420      1430      1440
CTCCGGGTAAATGAGTGCGACGGCGGGCAAGCCCCCGCTCCCCAGGCTCTCGGGGTCGCG
erProGlyLys
      450

1450      1460      1470      1480      1490      1500
CGAGGATGCTTGGCACGTACCCCGTGTACATACTTCCCGGGGCCCAGCATGGAAATAAA 1510      1520      1530      1540      1550      1560
GCACCCAGCGCTGCCCTGGGCCCCTGCAAAAAAAAAAAAAAAAAAAAAAAAAAAAAAAA

1570
AAAAAAAAAAAAAA
```

RECLONING TO E. coli EXPRESSION VECTOR

CONSTRUCTION OF L CHAIN EXPRESSING PLASMID

ANTI-HBS ANTIBODY GENES AND EXPRESSION PLASMIDS THEREFOR

TECHNICAL FIELD

This invention relates to anti-hepatitis B virus surface antigen (hereunder abbreviated as "HBs") antibody genes and expression plasmids therefor. More particularly, this invention relates to polynucleotides that respectively code for the L and H chains of a human anti-HBs antibody immunoglobulin and portions thereof, as well as expression plasmids containing those polynucleotides.

BACKGROUND ART

Hepatitis B virus is a dreadful source of infection which not only causes acute hepatitis by infection but also aggravates it, by continued infection, to irrecoverable chronic hepatitis, sometimes to cirrhosis and even to liver cancer. Three major types are known as antibodies against hepatitis B virus and they include an anti-HBs antibody, as well as an antibody against the core antigen (HBc) within the virus particle and an antibody against the e antigen (HBe) which is held to be contained in the core antigen. Among these three antibodies, the anti-HBs antibody has the hepatitis B virus neutralizing activity and, hence, it is expected to exhibit the phylactic effect against the virus and the ability to prevent induced manifestation of the disease and there exists a very strong demand that pharmaceutical preparations of the antibody be marketed as soon as possible.

However, producing pharmaceutical preparations of the anti-HBs antibody using human HBs antibody positive blood plasma as a starting material is subject to constraints on the starting material and, hence, is not practical. Monoclonal antibodies can be produced by using the cell fusion technique which has seen rapid developments in recent years but there are some doubts about the safety of the mouse derived antibody in administration to the human body. Furthermore, it is difficult to prepare a proliferative hybridoma that is stable for a sufficiently long time to achieve large-scale production of the human derived monoclonal antibody. Thus, none of the conventional techniques are capable of consistent supply of the human anti-HBs antibody as a pharmaceutical preparation.

DISCLOSURE OF INVENTION

The object of the present invention is to provide a technique by which a pharmaceutical preparation of the anti-HBs antibody that may safely be administered to the human body can be produced easily in a large amount and without any problems associated with the procurement of starting materials.

Thinking that the production of a human immunoglobulin with high titer and selectivity in microorganisms would be useful for the development of a pharmaceutical preparation of immunoglobulin for use in passive immunotherapy, the present inventors repeated intensive studies with a view to accomplishing large-scale production of the human monoclonal anti-HBs antibody in microorganisms. As a result, they succeeded in cloning human monoclonal anti-HBs antibody genes and expressing said genes by the recombination DNA technique. The present invention has been accomplished on the basis of this success.

Stated more specifically, the present invention relates to polynucleotides that code for the L and H chains of the human anti-HBs antibody immunoglobulin, as well as polynucleotides coding code for polypeptides that comprise portions of said L and H chains, respectively, which when expressed are reasonably effective in passive immunity (e.g., phylaxis against HB virus, prevention of manifestation of the disease and its treatment). The present invention also relates to plasmids that are capable expressing the L and H chain genes of the human anti-HBs antibody immunoglobulin and polypeptides that are reasonably effective in passive immunity, as well as expression plasmids containing said polynucleotides.

Screening for polypeptides that are reasonably effective in passive immunity can be readily accomplished by using a known assay technique such as enzyme immunoassay with the HBs antigen or passive hamagglutination test (a test kit such as "Hebsgencell" is commercially available from The Green Cross Corporation), with the anti-HBs titer being detected either qualitatively or quantitatively.

BRIEF DESCRIPTION OF DRAWINGS

FIG. 4 is a diagram showing the base sequence and L chain amino acid sequence of cDNA in pcK3061 (See SEQ. ID NOS:4 and 5);

FIG. 5 is a sequel to FIG. 4;

FIG. 6 is a diagram showing the base sequence and H chain amino acid sequence of cDNA in pcH2068 (See SEQ. ID NOS:6 and 7);

FIG. 7 is a sequel to FIG. 6;

FIG. 8 is a sequel to FIG. 7;

Figure 1A:
FIGS. 1a and 1b are diagrams showing the probes used in the hybridization of cDNAs coding for the L and H chains, respectively.

The polynucleotides of the present invention which code for the L and H chains of the human anti-HBs antibody immunoglobulin have been verified to have base sequences that are represented by the following formulae I and II respectively, as estimated from the sequence of the primary structure of cDNA that was cloned from the human anti-HBs antibody producing B cell line that was transformed with Epstein-Barr virus (hereunder abbreviated as EBV) (See SEQ. ID NOS:8 and 9):

Formula I

GACATCCAGATGACCCAGTCTCCATCTGCCATGGCTGCATCTGT
AGGAGACAGAGTCACCATCACTTGTCGGGCGAGTCAGGGCATT
GGCAATTATTTAGTCTGGTTTCAGCAGAAACCAGGGAAAGT
CCCTAAGCGCCTGATCTATGCTGCATCCAGTTTGCAAAGT
GGGGTCCCATCGAGGTTCAGCGGCAGTGGATCTGGGACAGAA
TTCACTCTCACAATCAGCAGACTGCAGCCTGAAGATTTTGCAAC
TTATTACTGTCTACATCATAATAATTACCCGCTAAGTTTCGGCGG
AGGGACCAAGGTGGAGATCAAACGAACTGTGGCTGCACCATCT
GTCTTCATCTTCCCGCCATCTGATGAGCAGTTGAAATCTGGAA
CTGCCTCTGTTGTGTGCCTGCTGAATAACTTCTATCCCAGAGAGG
CCAAAGTACAGTGGAAGGTGGATAACGCCCTCCAATCGGGTAA
CTCCCAGGAGAGTGTCACAGAGCAGGACAGCAAGGACAGCACC
TACAGCCTCAGCAGCACCCTGACGCTGAGCAAAGCAGACTAC
GAGAAACACAAAGTCTACGCCTGCAGAAGTCACCCATCAGGGC
CTGAGCTCGCCCGTCACAAAGAGCTTCAACAGGGGAGAAGTGT

Formula II

```
CAGGTGCAGCTGGTGGAGTCTGGGGGAGGCGTGGTCCAGCCT
GGGAGGTCCCTGAGACTCTCCTGTGCAGCCTCTGGATTCACCTT
CAGTAGCAATTCTATGCACTGGGTCCGCCAGGCTCCAGGCAA
GGGGTTGGAGTGGGTGGCAGTTATATTATATGATGGAAATCAT
AAATTCTACGCAGACTCCGTGAAGGGCCGATTCACCATTTCCAG
AGACAATTCCAAGAACACACTGTATCTGGAAGTGAAGAGCCTGC
AAACTGAGGACACGGGTGTCTATTACTGTATAAGAGATCAAAC
TTACGGAGTCCACAGATTTGACTCCTGGGGCCAGGGAACCCTGG
TCACCGTCTCCTCAGCCTCCACCAAGGGCCCATCGGTCTTCCCCC
TGGCACCCTCCTCCAAGAGCACCTCTGGGGGCACAGCGGCCT
GGGCTGCCTGGTCAAGGACTACTTCCCCGAACCGGTGACGGTGT
CGTGGAACTCAGGCGCCCTGGCCAGCGGCGTGCACACCTTCCC
GGCTGTCCTACAGTCCTCAGGACTCTACTCCCTCAGCAGCGTGG
TGACCGTGCCCTCCAGCAGCTTGGGCACCCAGACCTACATCTGC
AACGTGAATCACAAGCCCAGCAACACCAAGGTGGACAAGAAAG
TTGAGCCCAAATCTTGTGACAAAACTCACACATGCCCACCGTG
CCCAGCACCTGAACTCCTGGGGGGACCGTCAGTCTTCCTCTT
CCCCCCAAAACCCAAGGACACCCTCATGATCTCCCGGACCCCT
GAGGTCACATGCGTGGTGGTGGACGTGAGCCACGAAGACCCT
GAGGTCAAGTTCAACTGGTACGTGGACGGCGTGGAGGTGCATAA
TGCCAAGACAAAGCCGCGGGAGGAGCAGTACAACAGCACGTA
CCGGGTGGTCAGCGTCCTCACCGTCCTGCACCAGGACTGGCTG
AATGGCAAGGAGTACAAGTGCAAGGTCTCCAACAAAGCCCTCCC
AGCCCCCATCGAGAAAACCATCTCCAAAGCCAAAGGGCAG
CCCCGAGAACCACAGGTGTACACCCTGCCCCCATCCCGGGAT
GAGCTGACCAAGAACCAGGTCAGCCTGACCTGCCTGGTCAAAGG
CTTCTATCCCAGCGACATCGCCGTGGAGTGGGAGAGCAATGGG
CAGCCGGAGAACAACTACAAGACCACGCCTCCCGTGCTGGACT
CCGACGGCTCCTTCTTCCTCTACAGCAAGCTCACCGTGGACAA
GAGCAGGTGGCAGCAGGGGAACGTCTTCTCATGCTCCGTGATG
CATGAGGCTCTGCACAACCACTACACGCAGAAGAGCCTCTCCC
TGTCTCCGGGTAAA
```

The cloning of cDNA starts with the human anti-HBs antibody producing B cell line that has been transformed with EBV in a proliferative manner: mRNA is prepared by the usual procedure and a cDNA library is prepared and the desired cDNAs are obtained by hybridization with respective probes for the L and H chains and their base sequences are then determined.

Disclosed herein are the polynucleotides represented by formulae I and II as the nucleotide sequences of genes coding for the L and H chains of the anti-HBs antibody, but they are by no means intended to limit the polynucleotides of the present invention. Once the amino acid sequences of the L and H chains of the anti-HBs antibody are determined or once the amino acid sequences of polypeptides that are reasonably effective in passive immunity are designed, various nucleotide sequences that code for the same amino acid sequences can be designed and prepared on the basis of codon degeneracy. In this case, it is preferred to use codons that are used with high frequency by the host to be used.

When obtaining the anti-HBs antibody genes of the present invention, cDNA can be prepared by the procedures described in the examples that follow but this is by no means to be taken as limiting. Stated more specifically, if one nucleotide sequence that codes for the amino acid sequence of a native anti-HBs antibody is determined, the gene coding for this antibody can be cloned as cDNA by a strategy different from the one that is specifically described herein and, further, the gene can also be cloned from the genome of a cell that is capable of its production. In the case of cloning from the genome, the various primer nucleotides or probe nucleotides that were used in the examples that follow can be used as probes for the selection of genomic DNA fragments. Also usable are other probes that have been designed on the basis of the nucleotide sequence that is set forth in formula I or II. Common procedures for cloning the desired DNA from the genome are well known in the art (Current Protocols In Molecular Biology, John Wiley & Sons, Chapters 5 and 6).

The anti-HBs antibody coding genes of the present invention can also be prepared by chemical synthesis. The chemical synthesis of DNA can readily be done in the art adopting an automatic DNA synthesizer such as a 394 DNA/RNA synthesizer of Applied Biosystems.

The genes of the present invention which code for the anti-HBs antibody by codons different from indigenous codons, as well as genes coding for polypeptides that are reasonably effective in passive immunity can also be prepared by chemical synthesis as mentioned above; alternatively, they may be obtained by routine procedures such as site-directed mutagenesis using as a template the DNA or RNA that have the nucleotide sequence shown in formula I or II together with a mutagenic primer (see, for example, Current Protocols In Molecular Biology, John Wiley & Sons, Chapter 8).

The EBV transformed human anti-HBs antibody producing B cell line can be obtained by the following procedure: human peripheral blood lymphocytes are sensitized with EBV and the resulting transformed cells are cultured, the supernatant of the culture being selected by a known screening method using the antigen-antibody reaction with HBs, such as an enzyme immunoassay using an immobilized antigen.

In the next place, the thus prepared polynucleotides of the present invention are introduced as genes into plasmids and hosts such as *E. coli* are transformed by routine genetic recombination techniques so that they express not only the L and H chains but also polypeptides that are reasonably effective in passive immunity. The expressing of L and H chains and other polynucleotides of the present invention can be verified by immune precipitation with the anti-human IgG antibody. Introduction into plasmids, the establishment of transformed cell lines, the culture of those cell lines, and other operations can be performed in accordance with routine genetic recombination techniques.

Expression systems may be used as selected appropriately from those which are known to one skilled in the art but, if desired, the secretion efficiency and the amount of expression can be enhanced by the addition or modification of signal sequences or the selection of suitable hosts. Host cells are in no way limited but they include, for example, bacteria, yeasts and other fungi, the cultured cells of humans and other animals, and the cultured cells of plants.

Stated more specifically, the polynucleotides of the present invention are inserted as genes into appropriate expression vectors, which in turn are introduced into appropriate host cells, which are cultured and the desired anti-HBs antibody and its derivatives (e.g., polypeptides reasonably effective in passive immunity such as F(ab')$_2$, Fab, Fv, dAbs and H$_2$L$_2$) are collected from the resultant cultures (cells or media). The anti-HBs antibody and its derivatives may be obtained as biochemically or chemically modified, for example, N-terminus acylated.

Hosts may be either prokaryotic or eukaryotic organisms. Usable prokaryotic organisms are bacteria, especially *Escherichia coli* and genes bacillus such as *B. subtilis*. Usable eukaryotic organisms include: eukaryotic microorganisms such as yeasts as exemplified by those of the genus Saccharomyces, for example, *S. serevisiae;* insect cells such as *Spodoptera frugiperda,* Cabbage looper and *Bombyx mori;* animal cells such as human cells, monkey cells and mouse cells, especially mouse myeloma cells as exemplified by Sp2/0 (ATCC CRL1581) and p3×63.653–Ag8 (ATCC CRL1580).

Useful expression vectors include plasmids, phages, phagimids, and viruses [baculovirus (insect) and vaccinia virus (animal cell)]. The promoters in expression vectors are selected depending upon host cells; useful bacterial promoters include lac promoter, trp promoter, etc.; useful yeast promoters include adhl promoter, pqk promoter, etc. Exemplary insect promoters include baculovirus polyhedrin promoter, and exemplary animal cells include the early or late promoter of Simian Virus 40 (SV40) and the promoter of an antibody gene.

If enhancers are to be used, the enhancer of SV40, the enhancer of an antibody gene or the like are inserted either upstream or downstream of the gene to be expressed.

The polynucleotides of the present invention may be used to express the L and H chains within the single host cells to reconstruct the antibody molecule and this may be adopted as a routine procedure by one skilled in the art (see, for example, Nature (1991), 349, 293–299). When expressing antibody molecules that have been reconstructed using bacteria, especially E. coli, the anti-HBs antibody or its derivatives that can be produced include, for example, F(ab')$_2$ that lacks part of the constant region of the H chain (tetramer; see, for example, PNAS (1993), 90, 457–461), Fab (dimer; see, for example, Gene (1989), 85, 553–557; Science (1988), 240, 1041–1043; and PNAS (1993), 90, 457–461), as well as Fv which is composed of the variable regions of the L and H chains (dimer; see, Science (1988), 240, 1038–1041; Science (1988), 242, 423–426; and PNAS (1988), 85, 5879–5883), and dAbs which is solely composed of the variable region of the H chain (see, for example, Nature (1989), 341, 544–546).

When expressing antibody molecules that have been reconstructed using animal cells, especially myeloma cells, the anti-HBs antibody or its derivatives that can be produced include, for example, H$_2$L$_2$ (see, for example, Nature (1984), 312, 643–646), F(ab')$_2$ (tetramer; see, for example, Nature (1984), 312, 604–608), and Fv (dimer; see, for example, J.M.B. (1988), 203, 825–828).

The transformation of hosts with expression vectors can be accomplished by routine procedures that are well known in the art and some of these methods are described in Current Protocols In Molecular Biology, John Wiley & Sons. The culture of transformants can also be performed by conventional procedures.

The anti-HBs polypeptides can be purified from the cultures in accordance with conventional procedures for isolating and purifying proteins by, for example, ultrafiltration and various column chromatographic techniques such as chromatography on Sepharose.

It should be noted here that pcK3061 having cDNA coding for the L chain and pcH2068 having cDNA coding for the H chain each transform E. coli strain WA802 and the transformants were tagged with identifying designations Escherichia coli SBM326 and Escherichia coli SBM327 and deposited with the Fermentation Research Institute, the Agency of Industrial Science and Technology on Mar. 25, 1992 under respective accession numbers FERM P-12902 and FERM P-12903. Further, these transformants were transferred to International Deposition under the Budapest Treaty on Mar. 9, 1993 under respective accession numbers FERM BP-4229 and FERM BP-4230.

The following examples are provided for the purpose of further illustrating the present invention.

EXAMPLE 1

Cloning of Human Anti-HBs Antibody Genes

1) Preparation of mRNA
2) Preparation of cDNA
3) Screening for Anti-HBs L chain gene
4) Screening for Anti-HBs H chain gene
5) Analysis of the primary structural sequence of L chain gene
6) Analysis of the primary structural sequence of H chain gene
7) Characteristics of the primary structural sequences
1) Preparation of mRNA To pellets of ca. $6 \times 10^8$ anti-HBs antibody producing cells (ca. 1.5 g), 20 ml of Gua-SCN solution (4M Fluka puram grade Gua-SCN), 5% NaN-laurylsarcosine, 25 mM sodium citrate, 0.1M β-ME, and 0.1% Sigma Antifoam A were added and, after stirring on a vortex, the ingredients were completely mixed together in 5 min. Following the addition of 0.5 ml 1M acetic acid and 15 ml ethanol, the mixture was kept cold at −20° C. overnight and centrifuged at 8000 rpm for 10 min at −10° C. To the precipitate, 10 ml of Gua-HCl solution (7.5M Gua-HCl, 25 mM sodium citrate and 5 mM DTT) were added and dissolved completely. Following the addition of 0.5 ml of 1M acetic acid and 10 ml of ethanol, the solution was kept cold at −20° C. overnight and centrifuged to obtain an ethanol precipitate. These procedures were repeated once more. The centrifugal precipitate was suspend ed in a 70% ethanol-30% ETS solution (10 mM EDTA, 10 mM Tris-HCl (pH 7.4) and 0.5% SDS) and the suspension was centrifuged at 6000 rpm for 20 min at −10° C.; the centrifugal precipitate was dried with air.

The dried precipitate was dissolved in 3 ml of ETS solution and subjected to extraction with PC9 solution (a 24:24:1 mixed solution of phenol, chloroform and isoamyl alcohol as saturated with 10 mM Tris-HCl (pH 9), 100 mM NaCl and 2 mM EDTA solution). To the aqueous layer, sodium acetate (0.3M) in two volumes of ethanol was added and the fibrous DNA precipitate was wound up for removal while the remainder was kept cold at −20° C. overnight.

Following centrifugation at 10000 rpm for 30 min at −10° C., the centrifugal precipitate was washed with ethanol and stored at −20° C.

These procedures were repeated on two more batches of ca. $6 \times 10^8$ cells, finally yielding ca. 3.5 mg of RNA fractions from $1.8 \times 10^9$ cells.

To the RNA fractions, 5 ml of ETS solution and 0.7 ml of 4M LiCl solution were added and the mixture was loaded on an Oligo(dT) cellulose column (70 mg on a dry weight basis) The effluent was reloaded on the column to have the poly A RNA adsorbed. Thereafter, the column was washed with 45 ml of LETS solution (ETS solution containing 4M LiCl). Using 4.5 ml of ETS solution, poly A RNA (ca. 900 μg) was recovered and centrifuged to give a precipitate in ethanol. This centrifugal precipitate was dried lightly.

2) Preparation of cDNA (Step 1: Synthesis of cDNA)

The dried poly A RNA (ca. 900 μg) was dissolved in 105 μl of distilled water; to 15 μl (ca. 100 μg) of the solution, 15 μl of 5 mM Tris-HCl (pH 7.5) was added and the mixture was heat treated at 65° C. for 5 min, followed by warming at 37° C. Further, 7.5 μl of 8×RT buffer (400 mM Tris-HCl (pH 8.3, 37° C.), 64 mM MgCl$_2$, 240 mM KCl and 2.4 mM DTT), Okayama-Berg primer DNA (4.2 μl, 4.2 μg/2.1 pmole) and distilled water (1.3 μl) were added and the resulting liquid-mixture system (25 μl) was warmed at 37° C. for 5 min with 50 μCi of α-$^{32}$P-dCTP that had been solidified to dryness.

Further, 5 μl (75 U) of reverse transcriptase (Life Science) was added and the mixture was warmed at 37° C. for 45 min. To stop the reaction, 7.5 μl of 0.2M EDTA (pH 8.0) and 1.5 μl of 20% SDS were added. Following the addition of 69 μl of PC9, stirring on a vortex was conducted to give the aqueous layer. The PC9 layer was subjected to another extraction with 10 μl of 5 mM Tris-HCl (pH 7.5) to give the aqueous layer, which was added to the previously obtained aqueous layer to make a total volume of 80 μl. The combined aqueous layers were added to 80 μl of 4M NH$_4$OAc and 320 μl of ethanol and the mixture was cooled at −70° C. for 30 min. The tube was warmed with hands for thawing the frozen solution, which was then stirred on a vortex lightly and centrifuged at 10000 rpm for 10 min at 4° C. To the centrifugal precipitate, 30 μl of 5 mM Tris-HCl (pH 7.5) and 1 mM EDTA solution were added and, following the addition of 120 μl of ethanol, the mixture was kept cold at −70° C. overnight. After centrifugation, the precipitate was rinsed with 75% ethanol and solidified to dryness. When analyzed by 1% agarose neutral electrophoresis, the product was found to contain a measurable amount (⅔–¾) of RNA that was shorter than the 2.7 Kb primer vector but in a cDNA synthesis assay by autoradiography, only RNA that was longer than 2.7 Kb was observed.

(Step 2: Addition of dC chain)

To the cDNA precipitate as yielded in Step 1, 4.5 μl of 10×Cacodilate Tris buffer (1.4M Na-Cacodilate, 0.3M Tris-HCl (pH 6.8), 4.5 μl of 1 mM dCTP, 0.9 μl of 5 mM DTT and 6 μl of α-$^{32}$P-dCTP (60 μCi), 22.6 μl of distilled water and 4.5 μl of 10 mM CoCl$_2$ were added to make a 43-μl solution, which was warmed at 37° C. for 3 min. Following the addition of a terminal deoxynucleotidyl transferase (BRL) in an amount of 4 μl (60 U), the mixture was warmed at 37° C. for 10 min. After transfer to 0° C., 5.6 μl of 0.2M EDTA (pH 8.0) and 1 μl of 20% SDS were added and the mixture was subjected to extraction with 53.6 μl of PC9. The resulting PC9 layer was combined with the product of re-extraction with 10 μl of 5 mM Tris-HCl (pH 7.5) and 1 mM EDTA; to the combined PC9 layers, 64 μl of 4M NH$_4$OAc and 256 μl of ethanol were added to form a precipitate. To the precipitate, 30 μl of 4M NH$_4$OAc and 120 μl of ethanol were added to cause another precipitation; the thus obtained precipitate was rinsed with 75% ethanol and solidified to dryness.

(Step 3: Cleavage with HindIII)

To the DNA precipitate prepared in Step 2, 3 μl of 10×TA (330 mM Tris acetate (pH 7.9), 660 mM potassium acetate, 100 mM magnesium acetate and 5 mM DTT), 222 μl of distilled water and 5 μl (40 u) of restriction enzyme HindIII were added and reaction was conducted at 37° C. for 60 min. Following the addition of 3.75 μl of 0.2M EDTA and 0.75 μl of 20% SDS, extraction was conducted with 34.5 μl of PC9 and the PC9 layer was subjected to re-extraction with 10 μl of TE for subsequent addition. The aqueous layer was dissolved in ethanol and centrifuged; this procedure was repeated. The resulting centrifugal precipitate was solidified to dryness.

(Step 4: Circularization)

To the DNA precipitate prepared in Step 3, 30 μl of TE was added and to 5 μl (equivalent to 0.1 pmole) of the mixture, 2 μl (0.2 pmole) of linker DNA, 10 μl of 5×annealing buffer (50 mM Tris-HCl (pH 7.5), 5 mM EDTA and 0.5M NaCl) and 31.5 μl of distilled water were added. Following warming first at 65° C. for 5 min, then at 42° C. for 30 min and finally at room temperature for 30 min, the mixture was transferred to 0° C. Following the addition of 450 μl of a circularization buffer (20 mM Tris-HCl (pH 7.5), 4 mM MgCl$_2$, 10 mM (NH$_4$)$_2$SO$_4$, 0.1M KCl, 0.1 mM β-NAD and 50 μg/ml BSA) and 3 μl (3 μg) of E. coli ligase (PL) to make a total volume of 500 μl, the mixture was subjected to reaction at 12° C. overnight.

(Step 5: Conversion from RNA to DNA)

To 500 μl of the ligation mixture prepared in Step 4, 2 μl of 10 mM 4dNTP, 7.5 μl of 10 mM β-NAD, 2 μl (1 μg) of E. coli ligase (PL), 1 μl (1.7 μg) of DNA polymerase I, and 4 μl (4.8 U) of RNase H were added and reaction was carried out first at 12° C. for 1 h, then at 25° C. for 1 h. Thereafter, the reaction mixture was stored at 0° C.

(Step 6: Transformation)

Calcium-treated WA802 was transformed with 17 samples each consisting of 20 μl of the reaction solution prepared in Step 5. WA802 competent cells were prepared by the following procedure. A solution of cells that were cultured at 38° C. overnight in an LB broth (containing 10 g of bactotryptone, 5 g of yeast extract and 5 g of NaCl in 1 liter) was inoculated (1/50) into 60 ml of the LB broth and cultured at 37° C. to give an OD$_{660}$ value of 0.2. The cell suspension was quenched in ice for 5 min and centrifuged with a Beckman centrifuge JA20 at 5000 rpm for 5 min at 0° C. To the centrifugal precipitate, 30 ml of ice-cooled 50 mM CaCl$_2$-50 μg/ml thymidine solution were added to prepare a cell suspension, which was kept cold on ice for 5 min. Another centrifugation was conducted and 6 ml of an ice-cooled 50 mM CaCl$_2$-50 μg/ml thymidine solution were added to prepare a cell suspension, which was kept on ice for 10 min. The cooled suspension was divided in 0.3-ml portions among small test tubes for subsequent use.

A cDNA solution (20 μl) was added to each of the 0.3-ml portions of cell suspension, which were subsequently kept cold in ice water for 20 min, then warmed at 42° C. for 2 min. Following the addition of LB (2.7 ml), the mixtures were shaken at 37° C. for 40 min. Thereafter, every 0.3-ml portion of the mixture was inoculated on 10 LB (50 μg/ml Amp) plates and cultured at 37° C. overnight. As a result, ca. 8000 Ap$^r$ clones were prepared in each 20-μl portion of cDNA solution. About 5×10$^4$ Ap$^r$ clones were obtained from 8 samples of the cDNA solution and used in subsequent colony hybridization.

To the remaining 10 samples of the cDNA solution, 9 ml of LB was added and culture was done at 37° C. for 2 h. Thereafter, 100 μg/ml of Ap was added and culture was done overnight.

The culture was divided in 1-ml portions, which were stored in 40% glycerol at −20° C. Each sample contained 8000 clones, totalling 8×10$^4$ clones in 10 samples.

3) Screening for anti-HBs L chain gene

Before screening, 9 clones were selected at random and analyzed for the length of the inserted cDNA by means of PstI/PvuII; the length of cDNA fragments as detected ranged from the shortest zero to the longest 2.05 Kb. From the library of ca. 5×10$^4$ clones, 50 primary positive clones were obtained with genomic DNA pcK-1Sac-Sac (see FIG. 1a) being used as hybridization probe. Analysis after isolation and purification on LB Ap plates showed that all of the 50 clones were positive.

Figure 2A:
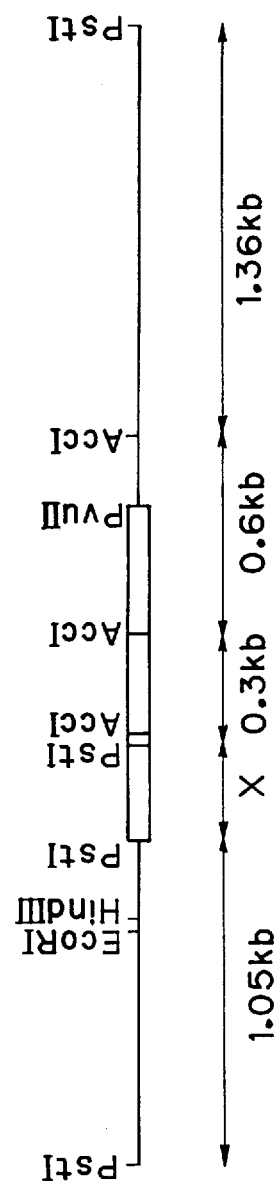
FIGS. 2a and 2b are schematic diagrams of cDNAs that code for the L and H chains, respectively.

For 35 of these clones, plasmid DNA was prepared and analyzed for the structure of cDNA by double digestion with restriction enzymes PstI and AccI. As FIG. 2a shows, the restriction enzyme cleavage sites in the vector portion and, if the Ck region were cloned, the AccI sites, are preserved and, hence, 1.36-Kb, 1.05-Kb and 0.6-Kb DNA fragments should be present in all clones. The length of 0.6-Kb fragments varies slightly with the length of poly A. In addition, a 0.3-Kb fragment and 0–0.33 Kb DNA fragments (as indicated by X) appear.

Figure 3:
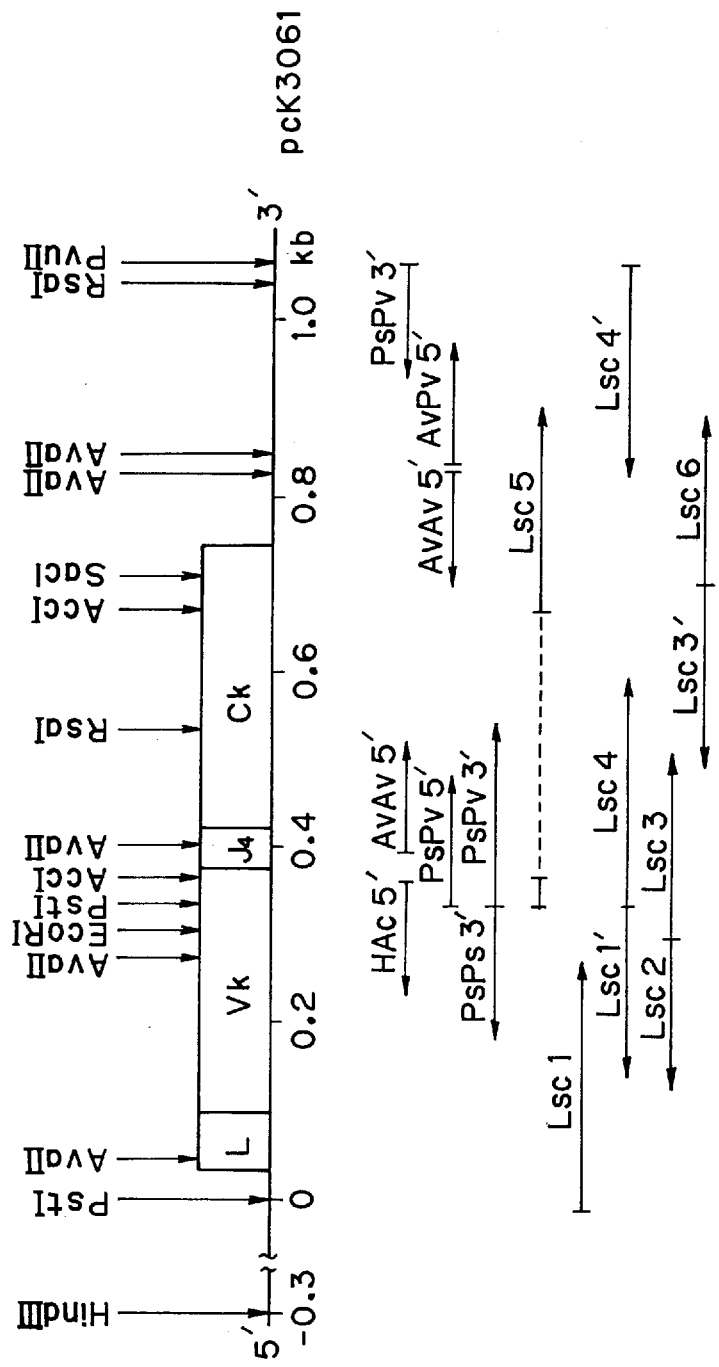
FIGS. 3a and 3b are physical maps of cloned cDNA pcK3061 and pcH2068 that code for L and H chains; respectively.

From the group of clones having the longest X (ca. 0.33 Kb) (i.e., pcK3061, pcK3151, pcK3191, pcK3192, pcK3201, pcK3461, pcK3471 and pcK3541), a single clone pcK3061 was selected (see FIG. 2A) and its physical map (see FIG. 3a) was constructed.

4) Screening for anti-HBs H chain gene

Figure 1B:
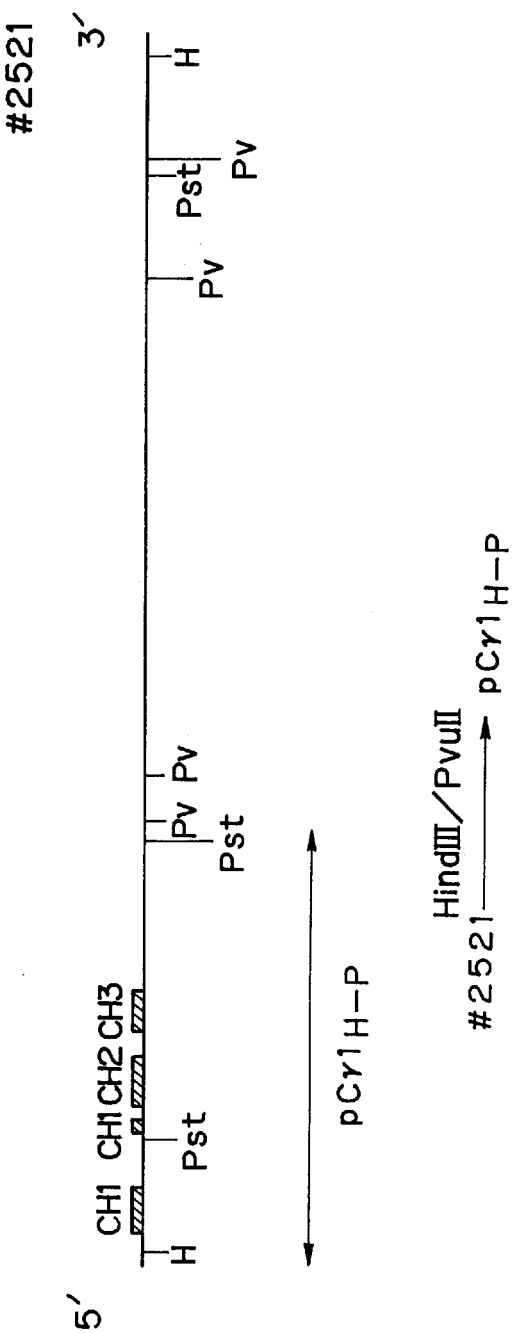

The anti-HBs-cDNA library of ca. $4 \times 10^4$ clones was treated to yield colonies of ca. $5 \times 10^4$ clones, which were subjected to colony hybridization with #2521 HindIII/PvuII 3 Kb DNA fragments (see FIG. 1b) being used as probe.

Figure 2B:
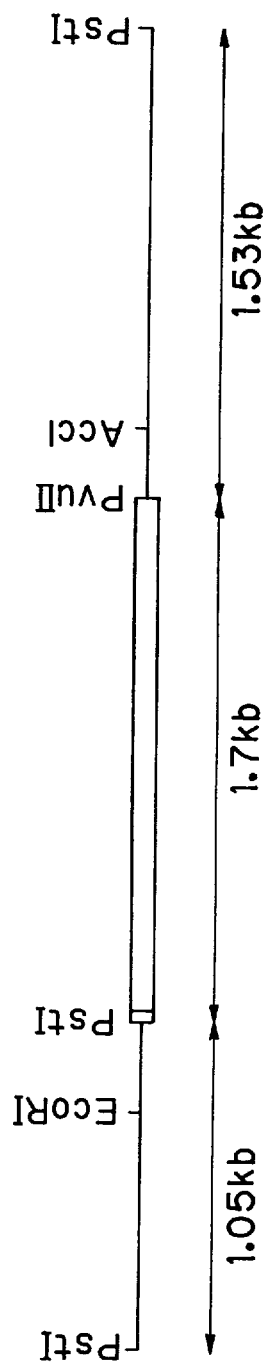
Figure 3B:
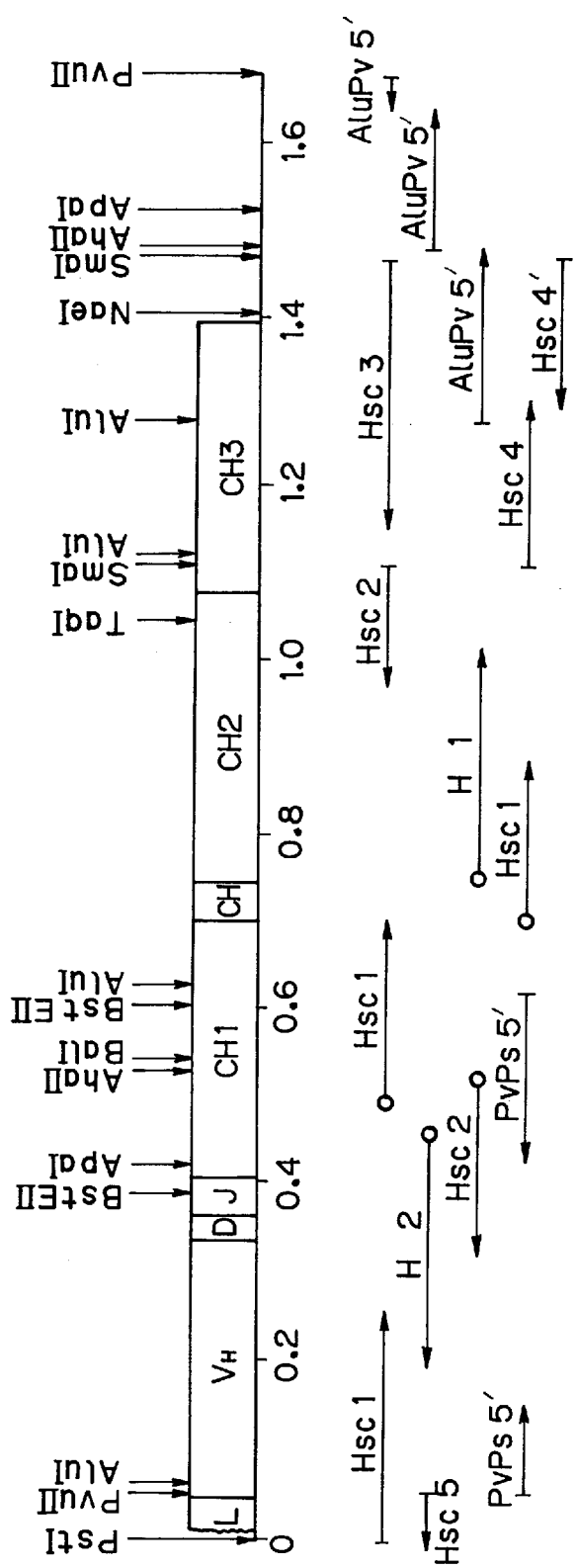
Figure 9:
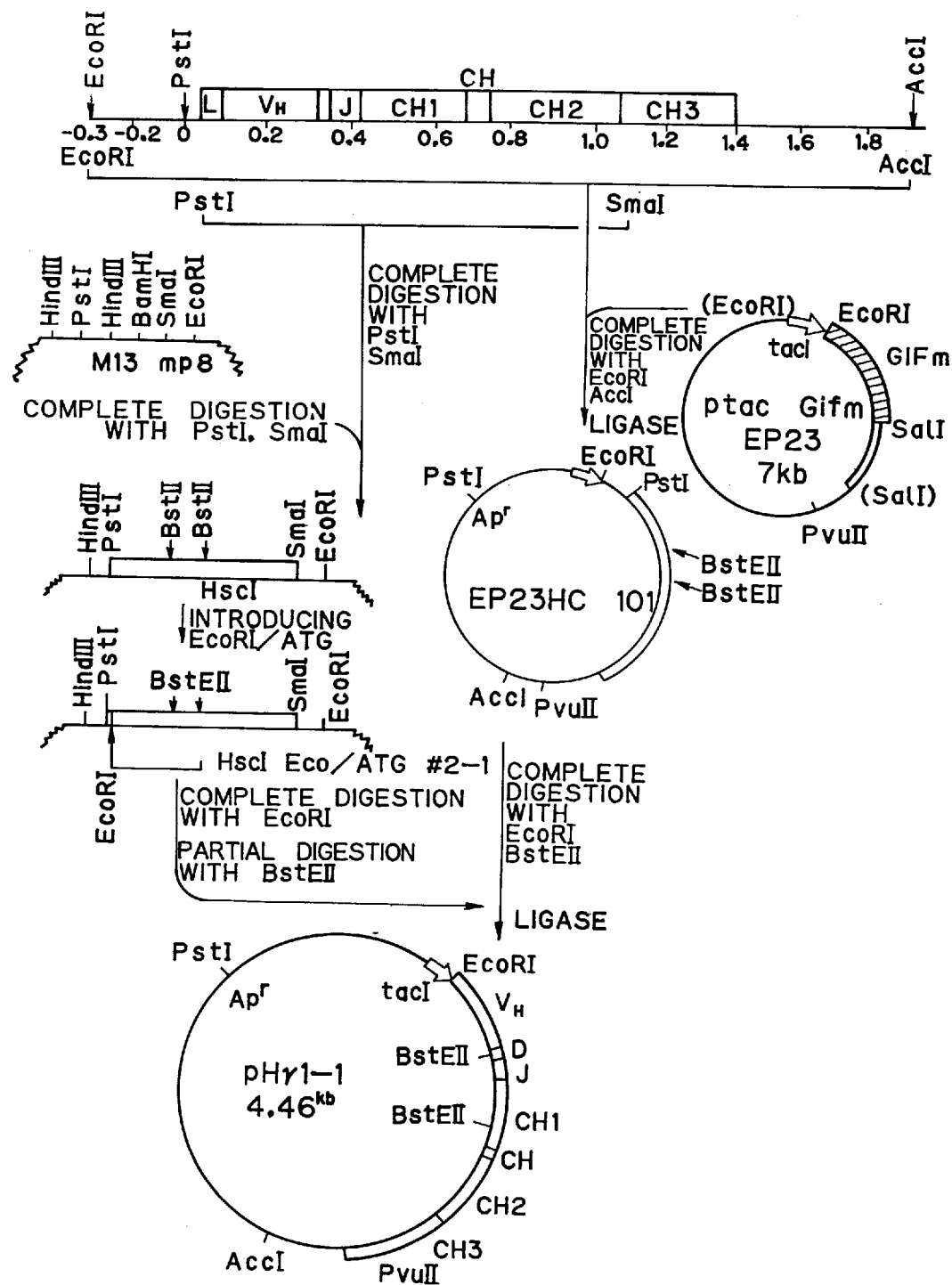
FIG. 9 is a diagram showing the steps of preparing pLk5B-1.
Figure 10:
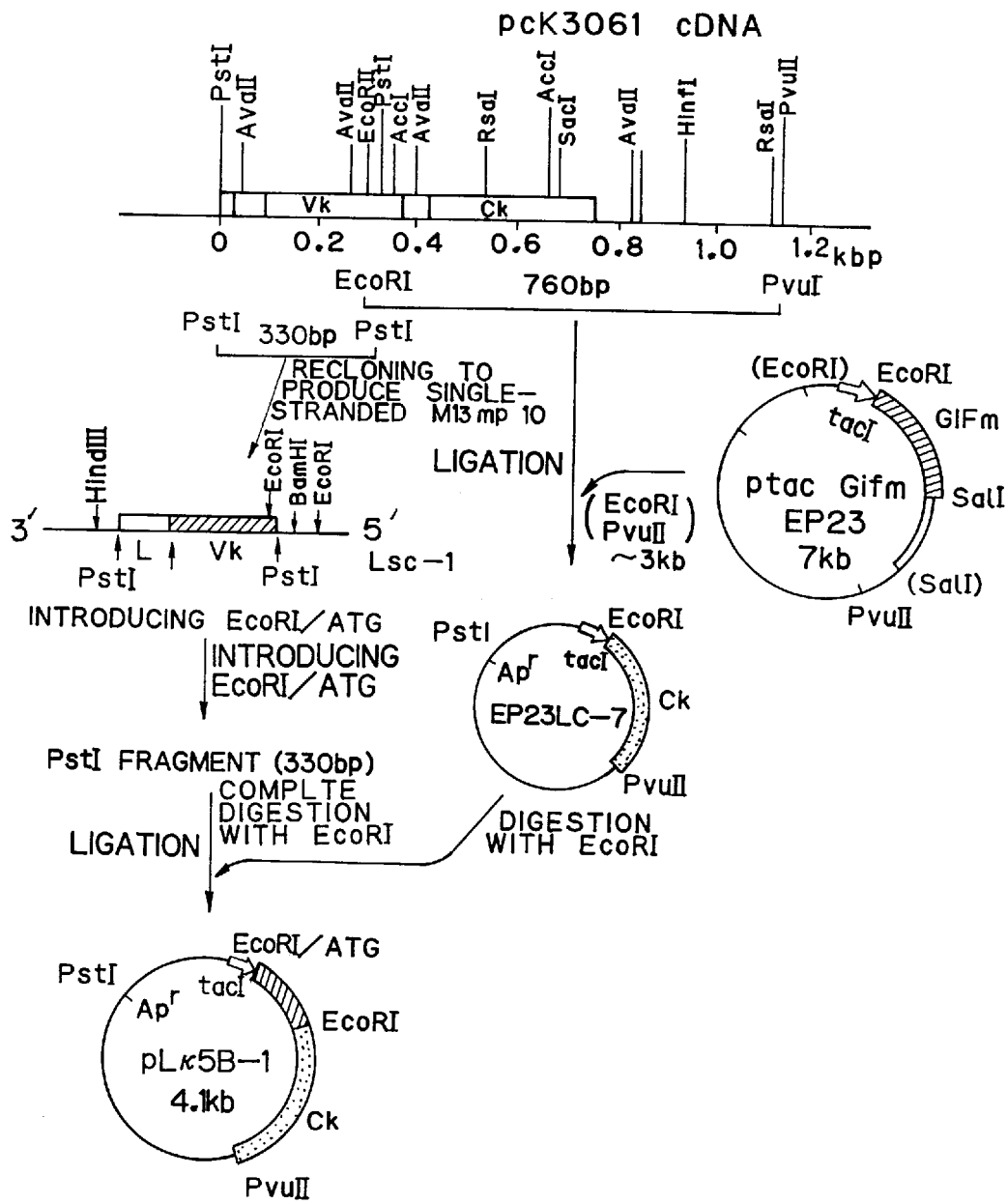
FIG. 10 is a diagram showing the steps of preparing pHγ1-1.

A total of 81 primary positive clones were obtained and 33 of them were strongly positive. These 33 clones were isolated and purified and DNA was prepared for 24 of them. Analysis for the length of the inserted cDNA by means of PstI/PvuII yielded a clone pCH2068 in which the length of the inserted cDNA fragment was ca. 1.7 Kb (see FIG. 2b) and its physical map was constructed (see FIG. 3b).

5) Analysis of the primary structural sequence of L chain gene

Sequencing of the L chain gene was conducted using pcK3061. The results are shown in FIGS. 4 and 5.

6) Analysis of the primary structural sequence of H chain gene

Sequencing of the H chain gene was conducted using pcH2068. The results are shown in FIGS. 6, 7 and 8.

7) characteristics of the primary structural sequences pcK3061

Having a total length of ca. 1040 bp, the cDNA consists of a 24 bp 5' untranslated region, a signal region coding for 22 amino acid residues, a V region coding for 108 amino acid residues, a C region coding for 106 amino acid residues, a 199 bp 3' untranslated region, and an ensuing poly A region of ca. 100 bp.

The L chain derived from this cDNA is of the κ type and was identified to be in subgroup I on the basis of the amino acid sequence of the V region. It was also found that JK4 was used as the J gene. The amino acid composition of the cDNA is shown in Table 1 for both the estimated and measured values.

pcH2068

Having a total length of ca. 1680 bp, the cDNA consists of a signal region coding for N-terminus deficient 9 amino acid residues, a V region coding for 120 amino acid residues, a C region coding for 330 amino acid residues, a 135 bp 3' untranslated region, and an ensuing poly A region of ca. 150 bp.

The H chain derived from this cDNA is of the γ1 type and was identified to be in subgroup III on the basis of the amino acid sequence of the V region. JH5 was used as the JH gene and the D region consisted of 24 bp. The amino acid composition of the cDNA is shown in Table 1 for both the estimated and measured values.

TABLE 1

| | L Chain | | H Chain | |
|---|---|---|---|---|
| | DNA sequence | Amino acid analysis | DNA sequence | Amino acid analysis |
| ASX | 16 | 16.65 | 38 | 40.1 |
| THR | 16 | 15.45 | 33 | 34.4 |
| SER | 29 | 29.72 | 53 | 51.4 |
| GLX | 23 | 22.68 | 39 | 39.9 |
| PRO | 11 | 11.71 | 33 | 33.9 |
| GLY | 15 | 17.77 | 31 | 35.0 |
| ALA | 14 | 14.70 | 19 | 25.2 |
| CYS | 5 | | 11 | |
| VAL | 16 | 15.63 | 48 | 44.1 |
| MET | 2 | 0.99 | 3 | |
| ILE | 7 | 6.63 | 8 | 7.4 |
| LEU | 15 | 15.00 | 35 | 35.0 |
| TYR | 9 | 8.40 | 18 | 71.1 |
| PHE | 9 | 9.02 | 15 | 16.2 |
| TRP | 2 | | 8 | |
| LYS | 13 | 12.87 | 33 | 30.7 |
| HIS | 4 | 4.10 | 12 | 11.2 |
| ARG | 8 | 6.74 | 13 | 12.7 |
| | 214 | | 450 | |

EXAMPLE 2

CONSTRUCTION OF EXPRESSION PLASMIDS

For expression in *E. coli*, restriction enzyme cleavage sites and ATG codon were introduced immediately after the signal sequence of cDNA of each of the H and L chains and, thereafter, ligation to a suitable promoter was conducted. Candidates for promoter include pL, pR, ptrp, plac, ptac, etc. but in this example ligation was conducted using ptacI promoter.

(L chain)

A PstI/PstI fragment (330 bp) of the L chain cDNA clone pcK3061 was recloned to the PstI site of M13mp10 (Boehringer Mannheim GmbH) to yield Lsc-1. To introduce an EcoRI cleavage site and ATG codon at the $V_\kappa N$ terminus of this clone, in vitro mutagenesis was conducted using a synthetic probe 33 mer (GGTTCCCAGGTGAATTCATGGACATCCAGATGA) (See SEQ. ID NO:1) and clone Lsc-1 Eco/ATG #19-4, in which a 216 bp band appeared on account of EcoRI digestion, was selected and its identity was verified by analysis of the primary structure.

In a separate step, a pcK3061 EcoRI/PvuII (760 bp) fragment was ligated with an EcoRI/PvuII (ca. 3 Kb) fragment of ptacI GIFmEP23 having the tacI promoter, thereby yielding EP23LC-7. The ptacI GIFmEP23 was constructed in accordance with the method described in Japanese Patent Public Disclosure (Kokai) No. Sho 60-54685 using a structural gene that was derived from the cDNA of human IFN-γ as prepared by the method disclosed by Gray et al. (Nature, 295, 503–508; 1982). Following digestion of EP23LC-7 with EcoRI, an EcoRI fragment (216 bp) of LscEco/ATG #19-4 was ligated to yield expression plasmid pLγ5B-1.

(H chain)

A PstI/SmaI fragment (1.1 Kb) of the H chain cDNA clone pcH2068 was recloned to the PstI/SmaI site of M13mp8 (Boehringer Mannheim GmbH) to yield Hsc-1. To introduce an EcoRI cleavage site and ATG codon at the $V_H$ N terminus of this clone, in vitro mutagenesis was conducted using synthetic DNA probe 33 mer (CTTTTAAGAGGTGAATTCATGCAGGTGCAGCTG) (See SEQ. ID NO:2) and clone Hsc-1Eco/ATG #2 and #19, in which a 1079 bp band appeared on account of EcoRI digestion, were selected and their secondary structures were verified by analysis of the primary structure.

In a separate step, an EcoRI/AccI fragment (2.1 Kb) of pcH2068 was ligated with an EcoRI/AccI fragment (2.65 Kb) of the plasmid ptac GIFmEP23 having the tacI promoter, thereby yielding EP23HC-101, -103 and -108. EP23HC-101 was digested completely with EcoRI/BstEII to yield a 3.9 Kb vector fragment, and Hsc-1Eco/ATG #2-1 was digested completely with EcoRI and partially with BstEII to slice a 572 bp fragment. The two fragments were ligated to yield expression plasmid pHγ 1-1.

EXAMPLE 3

EXPRESSING L AND H CHAINS

1) Ouchterlony analysis

Each of the L chain expressing plasmid pLk5B-1 and the H chain expression plasmid pHγ 1-1 was introduced into minicell producing *E. coli* strain P678-54 to produce a transformant. Minicells were prepared by the conventional procedure (Roosen K. J. et al., J. Bacteriol., 107, 21(1971)); thereafter, the proteins that were synthesized from the expression plasmids using a $^{14}$C-mixed amino acid solution (NEN, NEC-445E) were in vivo labelled and lysed with lysozyme (Sigma) and Brij58 (Sigma); thereafter, the supernatants of the minicells were recovered. An Ouchterlony test was conducted on the pHγ 1-1 transformant derived minicell produced protein using anti-human IgG (H+L) sheep serum, anti-human IgG (H+L) sheep serum and anti-human IgG (H+L) rabbit serum (all sera were available from Cappel); the protein was found to be positive. On the other hand, the host cells per se and the minicell produced proteins derived from EP23 transformant and Ep23HC-101 transformant were negative. It was therefore verified the H chain could be expressed in *E. coli*.

An Ouchterlony test was also conducted on the pLk5B-1 transformant derived minicell produced protein using anti-human IgG(k) rabbit serum (Miles and Cappel).

2) Analysis by SDS-polyacrylamide gel electrophoresis (PAGE)

The minicell produced protein derived from the H chain expressing plasmid pHγ 1-1 was subjected to immune precipitation using anti-human IgG (H+L) rabbit antibody (Cappel) as a primary antibody and protein A-Sepharose CL-4B (Pharmacia) as a secondary antibody; after 12% PAGE, analysis was done by autoradiography. Two bands appeared from the pHγ 1-1 derived transformant in the neighborhood of 45 KD but the result was negative with the EP23 transformant and EP23HC-101 transformant.

The L chain expressing plasmid pLk5B-1 derived minicell produced protein could not be detected by SDS-PAGE using the above-mentioned primary and secondary antibodies.

Hence, in order to introduce a restriction enzyme HindIII site about 25 bp downstream of the C terminus of the structural gene of the L chain cDNA, in vitro mutagenesis was effected using a synthetic probe 32 mer (GAAGTGCCCCCACAAGCTTCTCAGTTCCAGCC) (See SEQ. ID NO:3). Subsequently, the attenuator trpa DNA fragment in the *E. coli* tryptophan gene (Pharmacia) was inserted at the above-mentioned HindIII site and the correctness of its direction was verified by analysis of the primary structure. The thus prepared L chain expression plasmid pLk5B trpa was introduced into minicell producing strain P678-54 and an in vivo labelling experiment was conducted. As a result, a band appeared in the neighborhood of ca. 27 KD although it was hardly detectable in the pLk5B derived minicell produced protein. It was therefore verified that the L chain could be expressed in *E. coli*.

ADVANTAGE OF INVENTION

The present invention is beneficial not only for consistent and large-scale production of the anti-HBs antibody that can be administered safely to the human body but also for studies on the manufacture of antibodies that are improved from a genetic engineering viewpoint, as well as for their therapeutic applications.

---

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GGTTCCCAGG TGAATTCATG GACATCCAGA TGA 3 3

( 2 ) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CTTTTAAGAG GTGAATTCAT GCAGGTGCAG CTG                                           33

( 2 ) INFORMATION FOR SEQ ID NO:3:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GAAGTGCCCC CACAAGCTTC TCAGTTCCAG CC                                            32

( 2 ) INFORMATION FOR SEQ ID NO:4:

( i ) SEQUENCE CHARACTERISTICS:
        ( A ) LENGTH: 1066 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GGGGGGGGAA TCAGTCCCAC TCAGGACACA GCATGGACAT GAGGGTCCCC GCTCAGCTCC              60
TGGGGCTCCT GCTGCTCTGG TTCCCAGGTG CCAGGTGTGA CATCCAGATG ACCCAGTCTC              120
CATCTGCCAT GGCTGCATCT GTAGGAGACA GAGTCACCAT CACTTGTCGG GCGAGTCAGG              180
GCATTGGCAA TTATTTAGTC TGGTTTCAGC AGAAACCAGG GAAAGTCCCT AAGCGCCTGA              240
TCTATGCTGC ATCCAGTTTG CAAAGTGGGG TCCCATCGAG GTTCAGCGGC AGTGGATCTG              300
GGACAGAATT CACTCTCACA ATCAGCAGAC TGCAGCCTGA AGATTTTGCA ACTTATTACT              360
GTCTACATCA TAATAATTAC CCGCTAAGTT TCGGCGGAGG GACCAAGGTG GAGATCAAAC              420
GAACTGTGGC TGCACCATCT GTCTTCATCT TCCCGCCATC TGATGAGCAG TTGAAATCTG              480
GAACTGCCTC TGTTGTGTGC CTGCTGAATA ACTTCTATCC CAGAGAGGCC AAAGTACAGT              540
GGAAGGTGGA TAACGCCCTC CAATCGGGTA ACTCCCAGGA GAGTGTCACA GAGCAGGACA              600
GCAAGGACAG CACCTACAGC CTCAGCAGCA CCCTGACGCT GAGCAAAGCA GACTACGAGA              660
AACACAAAGT CTACGCCTGC GAAGTCACCC ATCAGGGCCT GAGCTCGCCC GTCACAAAGA              720
GCTTCAACAG GGGAGAGTGT TAGAGGGAGA AGTGCCCCCA CCTGCTCCTC AGTTCCAGCC              780
TGACCCCCTC CCATCCTTTG GCCTCTGACC CTTTTCCAC AGGGGACCTA CCCCTATTGC               840
GGTCCTCCAG CTCATCTTTC ACCTCACCCC CCTCCTCCTC CTTGGCTTTA ATTATGCTAA              900
TGTTGGAGGA GAATGAATAA ATAAAGTGAA TCTTTGCAAA AAAAAAAAAA AAAAAAAAA               960
AAAAAAAAAA AAAAAAAAAA AAAAAAAAAA AAAAAAAAAA AAAAAAAAAA AAAAAAAAAA              1020
AAAAAAAAAA AAAAAAAAAA GTACCTTCTG AGGCGGAAAG AACCAG                             1066

( 2 ) INFORMATION FOR SEQ ID NO:5:

( i ) SEQUENCE CHARACTERISTICS:
        ( A ) LENGTH: 236 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

| | | | | | | | | | | | | | | | |
|---|---|---|---|---|---|---|---|---|---|---|---|---|---|---|---|
|Met|Asp|Met|Arg|Val|Pro|Ala|Gln|Leu|Leu|Gly|Leu|Leu|Leu|Leu|Trp|
|1| | | |5| | | |10| | | | |15| | |
|Phe|Pro|Gly|Ala|Arg|Cys|Asp|Ile|Gln|Met|Thr|Gln|Ser|Pro|Ser|Ala|
| | | |20| | | |25| | | | |30| | | |
|Met|Ala|Ala|Ser|Val|Gly|Asp|Arg|Val|Thr|Ile|Thr|Cys|Arg|Ala|Ser|
| | |35| | | | |40| | | | |45| | | |
|Gln|Gly|Ile|Gly|Asn|Tyr|Leu|Val|Trp|Phe|Gln|Gln|Lys|Pro|Gly|Lys|
| |50| | | | |55| | | | |60| | | | |
|Val|Pro|Lys|Arg|Leu|Ile|Tyr|Ala|Ala|Ser|Ser|Leu|Gln|Ser|Gly|Val|
|65| | | | |70| | | | |75| | | | |80|
|Pro|Ser|Arg|Phe|Ser|Gly|Ser|Gly|Ser|Gly|Thr|Glu|Phe|Thr|Leu|Thr|
| | | | |85| | | | |90| | | | |95| |
|Ile|Ser|Arg|Leu|Gln|Pro|Glu|Asp|Phe|Ala|Thr|Tyr|Tyr|Cys|Leu|His|
| | | |100| | | | |105| | | | |110| | |
|His|Asn|Asn|Tyr|Pro|Leu|Ser|Phe|Gly|Gly|Gly|Thr|Lys|Val|Glu|Ile|
| | |115| | | | |120| | | | |125| | | |
|Lys|Arg|Thr|Val|Ala|Ala|Pro|Ser|Val|Phe|Ile|Phe|Pro|Pro|Ser|Asp|
| |130| | | | |135| | | | |140| | | | |
|Glu|Gln|Leu|Lys|Ser|Gly|Thr|Ala|Ser|Val|Val|Cys|Leu|Leu|Asn|Asn|
|145| | | | |150| | | | |155| | | | |160|
|Phe|Tyr|Pro|Arg|Glu|Ala|Lys|Val|Gln|Trp|Lys|Val|Asp|Asn|Ala|Leu|
| | | | |165| | | | |170| | | | |175| |
|Gln|Ser|Gly|Asn|Ser|Gln|Glu|Ser|Val|Thr|Glu|Gln|Asp|Ser|Lys|Asp|
| | | |180| | | | |185| | | | |190| | |
|Ser|Thr|Tyr|Ser|Leu|Ser|Ser|Thr|Leu|Thr|Leu|Ser|Lys|Ala|Asp|Tyr|
| | |195| | | | |200| | | | |205| | | |
|Glu|Lys|His|Lys|Val|Tyr|Ala|Cys|Glu|Val|Thr|His|Gln|Gly|Leu|Ser|
| |210| | | | |215| | | | |220| | | | |
|Ser|Pro|Val|Thr|Lys|Ser|Phe|Asn|Arg|Gly|Glu|Cys| | | | |
|225| | | | |230| | | | |235| | | | | |

( 2 ) INFORMATION FOR SEQ ID NO:6:

( i ) SEQUENCE CHARACTERISTICS:
        ( A ) LENGTH: 1576 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
GGGGGGGGGG GGTCGTTGGC CTTTTAAGAG GTGTCCAGTG TCAGGTGCAG CTGGTGGAGT      60
CTGGGGGAGG CGTGGTCCAG CCTGGGAGGT CCCTGAGACT CTCCTGTGCA GCCTCTGGAT     120
TCACCTTCAG TAGCAATTCT ATGCACTGGG TCCGCCAGGC TCCAGGCAAG GGGTTGGAGT     180
GGGTGGCAGT TATATTATAT GATGGAAATC ATAAATTCTA CGCAGACTCC GTGAAGGGCC     240
GATTCACCAT TTCCAGAGAC AATTCCAAGA ACACACTGTA TCTGGAAGTG AAGAGCCTGC     300
AAACTGAGGA CACGGGTGTC TATTACTGTA TAAGAGATCA AACTTACGGA GTCCACAGAT     360
TTGACTCCTG GGGCCAGGGA ACCCTGGTCA CCGTCTCCTC AGCCTCCACC AAGGGCCCAT     420
CGGTCTTCCC CCTGGCACCC TCCTCCAAGA GCACCTCTGG GGGCACAGCG GCCCTGGGCT     480
GCCTGGTCAA GGACTACTTC CCCGAACCGG TGACGGTGTC GTGGAACTCA GGCGCCCTGG     540
CCAGCGGCGT GCACACCTTC CCGGCTGTCC TACAGTCCTC AGGACTCTAC TCCCTCAGCA     600
GCGTGGTGAC CGTGCCCTCC AGCAGCTTGG GCACCCAGAC CTACATCTGC AACGTGAATC     660
```

-continued

```
ACAAGCCCAG  CAACACCAAG  GTGGACAAGA  AAGTTGAGCC  CAAATCTTGT  GACAAAACTC      720
ACACATGCCC  ACCGTGCCCA  GCACCTGAAC  TCCTGGGGGG  ACCGTCAGTC  TTCCTCTTCC      780
CCCCAAAACC  CAAGGACACC  CTCATGATCT  CCCGGACCCC  TGAGGTCACA  TGCGTGGTGG      840
TGGACGTGAG  CCACGAAGAC  CCTGAGGTCA  AGTTCAACTG  GTACGTGGAC  GGCGTGGAGG      900
TGCATAATGC  CAAGACAAAG  CCGCGGGAGG  AGCAGTACAA  CAGCACGTAC  CGGGTGGTCA      960
GCGTCCTCAC  CGTCCTGCAC  CAGGACTGGC  TGAATGGCAA  GGAGTACAAG  TGCAAGGTCT     1020
CCAACAAAGC  CCTCCCAGCC  CCCATCGAGA  AAACCATCTC  CAAAGCCAAA  GGGCAGCCCC     1080
GAGAACCACA  GGTGTACACC  CTGCCCCCAT  CCCGGGATGA  GCTGACCAAG  AACCAGGTCA     1140
GCCTGACCTG  CCTGGTCAAA  GGCTTCTATC  CAGCGACAT  CGCCGTGGAG  TGGGAGAGCA     1200
ATGGGCAGCC  GGAGAACAAC  TACAAGACCA  CGCCTCCCGT  GCTGGACTCC  GACGGCTCCT     1260
TCTTCCTCTA  CAGCAAGCTC  ACCGTGGACA  AGAGCAGGTG  GCAGCAGGGG  AACGTCTTCT     1320
CATGCTCCGT  GATGCATGAG  GCTCTGCACA  ACCACTACAC  GCAGAAGAGC  CTCTCCCTGT     1380
CTCCGGGTAA  ATGAGTGCGA  CGGCCGGCAA  GCCCCGCTC   CCCAGGCTCT  CGGGGTCGCG     1440
CGAGGATGCT  TGGCACGTAC  CCCGTGTACA  TACTTCCCGG  GCGCCCAGCA  TGGAAATAAA     1500
GCACCCAGCG  CTGCCCTGGG  CCCCTGCAAA  AAAAAAAAAA  AAAAAAAAAA  AAAAAAAAAA     1560
AAAAAAAAAA  AAAAA                                                          1576
```

( 2 ) INFORMATION FOR SEQ ID NO:7:

( i ) SEQUENCE CHARACTERISTICS:
        ( A ) LENGTH: 459 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Val Gly Leu Leu Arg Gly Val Gln Cys Gln Val Gln Leu Val Glu Ser
 1               5                  10                  15

Gly Gly Gly Val Val Gln Pro Gly Arg Ser Leu Arg Leu Ser Cys Ala
                20                  25                  30

Ala Ser Gly Phe Thr Phe Ser Ser Asn Ser Met His Trp Val Arg Gln
            35                  40                  45

Ala Pro Gly Lys Gly Leu Glu Trp Val Ala Val Ile Leu Tyr Asp Gly
        50                  55                  60

Asn His Lys Phe Tyr Ala Asp Ser Val Lys Gly Arg Phe Thr Ile Ser
65                  70                  75                  80

Arg Asp Asn Ser Lys Asn Thr Leu Tyr Leu Glu Val Lys Ser Leu Gln
                85                  90                  95

Thr Glu Asp Thr Gly Val Tyr Tyr Cys Ile Arg Asp Gln Thr Tyr Gly
                100                 105                 110

Val His Arg Phe Asp Ser Trp Gly Gln Gly Thr Leu Val Thr Val Ser
            115                 120                 125

Ser Ala Ser Thr Lys Gly Pro Ser Val Phe Pro Leu Ala Pro Ser Ser
        130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Ala
                165                 170                 175

Ser Gly Val His Thr Phe Pro Ala Val Leu Gln Ser Ser Gly Leu Tyr
                180                 185                 190
```

```
Ser  Leu  Ser  Ser  Val  Val  Thr  Val  Pro  Ser  Ser  Ser  Leu  Gly  Thr  Gln
          195                      200                     205

Thr  Tyr  Ile  Cys  Asn  Val  Asn  His  Lys  Pro  Ser  Asn  Thr  Lys  Val  Asp
     210                      215                     220

Lys  Lys  Val  Glu  Pro  Lys  Ser  Cys  Asp  Lys  Thr  His  Thr  Cys  Pro  Pro
225                      230                     235                          240

Cys  Pro  Ala  Pro  Glu  Leu  Leu  Gly  Gly  Pro  Ser  Val  Phe  Leu  Phe  Pro
                    245                     250                          255

Pro  Lys  Pro  Lys  Asp  Thr  Leu  Met  Ile  Ser  Arg  Thr  Pro  Glu  Val  Thr
               260                 265                     270

Cys  Val  Val  Val  Asp  Val  Ser  His  Glu  Asp  Pro  Glu  Val  Lys  Phe  Asn
          275                      280                     285

Trp  Tyr  Val  Asp  Gly  Val  Glu  Val  His  Asn  Ala  Lys  Thr  Lys  Pro  Arg
     290                      295                     300

Glu  Glu  Gln  Tyr  Asn  Ser  Thr  Tyr  Arg  Val  Val  Ser  Val  Leu  Thr  Val
305                      310                     315                          320

Leu  His  Gln  Asp  Trp  Leu  Asn  Gly  Lys  Glu  Tyr  Lys  Cys  Lys  Val  Ser
                    325                     330                          335

Asn  Lys  Ala  Leu  Pro  Ala  Pro  Ile  Glu  Lys  Thr  Ile  Ser  Lys  Ala  Lys
               340                 345                     350

Gly  Gln  Pro  Arg  Glu  Pro  Gln  Val  Tyr  Thr  Leu  Pro  Pro  Ser  Arg  Asp
          355                      360                     365

Glu  Leu  Thr  Lys  Asn  Gln  Val  Ser  Leu  Thr  Cys  Leu  Val  Lys  Gly  Phe
     370                      375                     380

Tyr  Pro  Ser  Asp  Ile  Ala  Val  Glu  Trp  Glu  Ser  Asn  Gly  Gln  Pro  Glu
385                      390                     395                          400

Asn  Asn  Tyr  Lys  Thr  Thr  Pro  Pro  Val  Leu  Asp  Ser  Asp  Gly  Ser  Phe
                    405                     410                          415

Phe  Leu  Tyr  Ser  Lys  Leu  Thr  Val  Asp  Lys  Ser  Arg  Trp  Gln  Gln  Gly
               420                 425                     430

Asn  Val  Phe  Ser  Cys  Ser  Val  Met  His  Glu  Ala  Leu  His  Asn  His  Tyr
          435                      440                     445

Thr  Gln  Lys  Ser  Leu  Ser  Leu  Ser  Pro  Gly  Lys
     450                      455
```

(2) INFORMATION FOR SEQ ID NO:8:

(i) SEQUENCE CHARACTERISTICS:
        (A) LENGTH: 642 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
GACATCCAGA  TGACCCAGTC  TCCATCTGCC  ATGGCTGCAT  CTGTAGGAGA  CAGAGTCACC    60
ATCACTTGTC  GGGCGAGTCA  GGGCATTGGC  AATTATTTAG  TCTGGTTTCA  GCAGAAACCA   120
GGGAAAGTCC  CTAAGCGCCT  GATCTATGCT  GCATCCAGTT  TGCAAAGTGG  GGTCCCATCG   180
AGGTTCAGCG  GCAGTGGATC  TGGGACAGAA  TTCACTCTCA  CAATCAGCAG  ACTGCAGCCT   240
GAAGATTTTG  CAACTTATTA  CTGTCTACAT  CATAATAATT  ACCCGCTAAG  TTTCGGCGGA   300
GGGACCAAGG  TGGAGATCAA  ACGAACTGTG  GCTGCACCAT  CTGTCTTCAT  CTTCCCGCCA   360
TCTGATGAGC  AGTTGAAATC  TGGAACTGCC  TCTGTTGTGT  GCCTGCTGAA  TAACTTCTAT   420
CCCAGAGAGG  CCAAAGTACA  GTGGAAGGTG  GATAACGCCC  TCCAATCGGG  TAACTCCCAG   480
```

```
GAGAGTGTCA  CAGAGCAGGA  CAGCAAGGAC  AGCACCTACA  GCCTCAGCAG  CACCCTGACG    540

CTGAGCAAAG  CAGACTACGA  GAAACACAAA  GTCTACGCCT  GCGAAGTCAC  CCATCAGGGC    600

CTGAGCTCGC  CCGTCACAAA  GAGCTTCAAC  AGGGGAGAGT  GT                         642
```

( 2 ) INFORMATION FOR SEQ ID NO:9:

( i ) SEQUENCE CHARACTERISTICS:
        ( A ) LENGTH: 1350 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
CAGGTGCAGC  TGGTGGAGTC  TGGGGGAGGC  GTGGTCCAGC  CTGGGAGGTC  CCTGAGACTC     60

TCCTGTGCAG  CCTCTGGATT  CACCTTCAGT  AGCAATTCTA  TGCACTGGGT  CCGCCAGGCT    120

CCAGGCAAGG  GGTTGGAGTG  GGTGGCAGTT  ATATTATATG  ATGGAAATCA  TAAATTCTAC    180

GCAGACTCCG  TGAAGGGCCG  ATTCACCATT  TCCAGAGACA  ATTCCAAGAA  CACACTGTAT    240

CTGGAAGTGA  AGAGCCTGCA  AACTGAGGAC  ACGGGTGTCT  ATTACTGTAT  AAGAGATCAA    300

ACTTACGGAG  TCCACAGATT  TGACTCCTGG  GGCCAGGGAA  CCCTGGTCAC  CGTCTCCTCA    360

GCCTCCACCA  AGGGCCCATC  GGTCTTCCCC  CTGGCACCCT  CCTCCAAGAG  CACCTCTGGG    420

GGCACAGCGG  CCCTGGGCTG  CCTGGTCAAG  GACTACTTCC  CCGAACCGGT  GACGGTGTCG    480

TGGAACTCAG  GCGCCCTGGC  CAGCGGCGTG  CACACCTTCC  CGGCTGTCCT  ACAGTCCTCA    540

GGACTCTACT  CCCTCAGCAG  CGTGGTGACC  GTGCCCTCCA  GCAGCTTGGG  CACCCAGACC    600

TACATCTGCA  ACGTGAATCA  CAAGCCCAGC  AACACCAAGG  TGGACAAGAA  AGTTGAGCCC    660

AAATCTTGTG  ACAAAACTCA  CACATGCCCA  CCGTGCCCAG  CACCTGAACT  CCTGGGGGGA    720

CCGTCAGTCT  TCCTCTTCCC  CCCAAAACCC  AAGGACACCC  TCATGATCTC  CCGGACCCCT    780

GAGGTCACAT  GCGTGGTGGT  GGACGTGAGC  CACGAAGACC  CTGAGGTCAA  GTTCAACTGG    840

TACGTGGACG  GCGTGGAGGT  GCATAATGCC  AAGACAAAGC  CGCGGGAGGA  GCAGTACAAC    900

AGCACGTACC  GGGTGGTCAG  CGTCCTCACC  GTCCTGCACC  AGGACTGGCT  GAATGGCAAG    960

GAGTACAAGT  GCAAGGTCTC  CAACAAAGCC  CTCCCAGCCC  CCATCGAGAA  AACCATCTCC   1020

AAAGCCAAAG  GGCAGCCCCG  AGAACCACAG  GTGTACACCC  TGCCCCCATC  CCGGGATGAG   1080

CTGACCAAGA  ACCAGGTCAG  CCTGACCTGC  CTGGTCAAAG  GCTTCTATCC  CAGCGACATC   1140

GCCGTGGAGT  GGGAGAGCAA  TGGGCAGCCG  GAGAACAACT  ACAAGACCAC  GCCTCCCGTG   1200

CTGGACTCCG  ACGGCTCCTT  CTTCCTCTAC  AGCAAGCTCA  CCGTGGACAA  GAGCAGGTGG   1260

CAGCAGGGGA  ACGTCTTCTC  ATGCTCCGTG  ATGCATGAGG  CTCTGCACAA  CCACTACACG   1320

CAGAAGAGCC  TCTCCCTGTC  TCCGGGTAAA                                      1350
```

We claim:

1. A polynucleotide consisting essentially of the base sequence of the following polynucleotide or a polynucleotide coding for a polypeptide encoded thereby:

```
GACATCCAGATGACCCAGTCTCCATCTGCCATGGCTGCATCTGT
AGGAGACAGAGTCACCATCACTTGTCGGGCGAGTCAGGGCATT
GGCAATTATTTAGTCTGGTTTCAGCAGAAACCAGGGAAAGT
CCCTAAGCGCCTGATCTATGCTGCATCCAGTTTGCAAAGT
GGGGTCCCATCGAGGTTCAGCGGCAGTGGATCTGGGACAGAA
TTCACTCTCACAATCAGCAGACTGCAGCCTGAAGATTTTGCAAC
TTATTACTGTCTACATCATAATAATTACCCGCTAAGTTTCGGCGG
AGGGACCAAGGTGGAGATCAAACGAACTGTGGCTGCACCATCT
GTCTTCATCTTCCCGCCATCTGATGAGCAGTTGAAATCTGGAA
CTGCCTCTGTTGTGTGCCTGCTGAATAACTTCTATCCCAGAGAGG
CCAAAGTACAGTGGAAGGTGGATAACGCCCTCCAATCGGGTAA
CTCCCAGGAGAGTGTCACAGAGCAGGACAGCAAGGACAGCACC
TACAGCCTCAGCAGCACCCTGACGCTGAGCAAAGCAGACTAC
GAGAAACACAAAGTCTACGCCTGCAGAAGTCACCCATCAGGGC
CTGAGCTCGCCCGTCACAAAGAGCTTCAACAGGGGAGAAGTGT
``` which polynucleotide contains the variable region of the L-chain derived from a human anti-HBs antibody.

2. A polynucleotide consisting essentially of the base sequence of the following polynucleotide or a polynucleotide coding for a polypeptide encoded thereby:

CAGGTGCAGCTGGTGGAGTCTGGGGGAGGCGTGGTCCAGCCT
GGGAGGTCCCTGAGACTCTCCTGTGCAGCCTCTGGATTCACCTT
CAGTAGCAATTCTATGCACTGGGTCCGCCAGGCTCCAGGCAA
GGGGTTGGAGTGGGTGGCAGTTATATTATATGATGGAAATCAT
AAATTCTACGCAGACTCCGTGAAGGGCCGATTCACCATTTCCAG
AGACAATTCCAAGAACACACTGTATCTGGAAGTGAAGAGCCTGC
AAACTGAGGACACGGGTGTCTATTACTGTATAAGAGATCAAAC
TTACGGAGTCCACAGATTTGACTCCTGGGGCCAGGGAACCCTGG
TCACCGTCTCCTCAGCCTCCACCAAGGGCCCATCGGTCTTCCCCC
TGGCACCCTCCTCCAAGAGCACCTCTGGGGGCACAGCGGCCCT
GGGCTGCCTGGTCAAGGACTACTTCCCCGAACCGGTGACGGTGT
CGTGGAACTCAGGCGCCCTGGCCAGCGGCGTGCACACCTTCCC
GGCTGTCCTACAGTCCTCAGGACTCTACTCCCTCAGCAGCGTGG
TGACCGTGCCCTCCAGCAGCTTGGGCACCCAGACCTACATCTGC
AACGTGAATCACAAGCCCAGCAACACCAAGGTGGACAAGAAAG
TTGAGCCCAAATCTTGTGACAAAACTCACACATGCCCACCGTG
CCCAGCACCTGAACTCCTGGGGGGACCGTCAGTCTTCCTCTT
CCCCCCAAAACCCAAGGACACCCTCATGATCTCCCGGACCCCT

-continued

GAGGTCACATGCGTGGTGGTGGACGTGAGCCACGAAGACCCT
GAGGTCAAGTTCAACTGGTACGTGGACGGCGTGGAGGTGCATAA
TGCCAAGACAAAGCCGCGGGAGGAGCAGTACAACAGCACGTA
CCGGGTGGTCAGCGTCCTCACCGTCCTGCACCAGGACTGGCTG
AATGGCAAGGAGTACAAGTGCAAGGTCTCCAACAAAGCCCTCCC
AGCCCCCATCGAGAAAACCATCTCCAAAGCCAAAGGGCAG
CCCCGAGAACCACAGGTGTACACCCTGCCCCCATCCCGGGAT
GAGCTGACCAAGAACCAGGTCAGCCTGACCTGCCTGGTCAAAGG
CTTCTATCCCAGCGACATCGCCGTGGAGTGGGAGAGCAATGGG
CAGCCGGAGAACAACTACAAGACCACGCCTCCCGTGCTGGACT
CCGACGGCTCCTTCTTCCTCTACAGCAAGCTCACCGTGGACAA
GAGCAGGTGGCAGCAGGGGAACGTCTTCTCATGCTCCGTGATG
CATGAGGCTCTGCACAACCACTACACGCAGAAGAGCCTCTCCC
TGTCTCCGGGTAAA which polynucleotide contains the variable region of the H-chain derived from a human anti-HBs antibody.

3. An expression plasmid containing the polynucleotide recited in claim 1.

4. An expression plasmid containing the polynucleotide recited in claim 2.

* * * * *